United States Patent [19]

Bernstein

[11] Patent Number: 4,543,327
[45] Date of Patent: * Sep. 24, 1985

[54] MALATE DEHYDROGENASE METHOD

[76] Inventor: Larry H. Bernstein, 1725 Campus Dr., Binghamton, N.Y. 13903

[*] Notice: The portion of the term of this patent subsequent to Jan. 19, 1999 has been disclaimed.

[21] Appl. No.: 431,028

[22] Filed: Sep. 30, 1982

Related U.S. Application Data

[63] Continuation-in-part of Ser. No. 340,132, Jan. 19, 1982, abandoned, which is a continuation of Ser. No. 158,121, Jun. 10, 1980, Pat. No. 4,311,791.

[51] Int. Cl.$^4$ ............................................. C12Q 1/32
[52] U.S. Cl. ..................................................... 435/26
[58] Field of Search ................. 435/26, 291, 805, 810, 435/184

[56] References Cited

U.S. PATENT DOCUMENTS

| | | | |
|---|---|---|---|
| 3,862,010 | 1/1975 | Rush et al. | 436/26 |
| 4,266,022 | 5/1981 | Lamprecht | 435/26 |
| 4,311,791 | 1/1982 | Bernstein | 435/26 |

Primary Examiner—Esther M. Kepplinger
Attorney, Agent, or Firm—Dale R. Lovercheck; Charles L. Lovercheck; Wayne L. Lovercheck

[57] ABSTRACT

A diagnostic method is disclosed, based on the automated kinetic determination of LD and MD isoenzymes in serum, which utilizes the comparison of two rates of LD and MD activity at different concentrations of substrate. It compares the first activity to the second concentration (activity) to obtain a ratio of activities relative to the two said activities with the first activity in the denominator and the second activity in the numerator and then determining the amount of MD activity enhancement (accelerated activity) by observing the ratio of measured MD activity.

5 Claims, No Drawings

MALATE DEHYDROGENASE METHOD

REFERENCE TO PRIOR PATENTS AND APPLICATIONS

This case is a continuation in part of application Ser. No. 340,132, filed Jan. 19, 1982, now abandoned, which was a continuation of application Ser. No. 158,121, filed June 10, 1980 now issued as U.S. Pat. No. 4,311,791.

REFERENCE OF PRIOR ART

U.S. Pat. No. 3,862,010 issued Jan. 21, 1975.
U.S. Pat. No. 4,003,795 issued Jan. 18, 1977.
Publication cited in U.S. Pat. No. 4,311,791.

The method disclosed herein is applicable to automated instruments which is a heretofore unanswered need in the art as noted by the Wilkinson reference cited in U.S. Pat. No. 4,003,795. This need is answered by the elimination of the preincubation step required in previous methods.

INTRODUCTION

Malate dehydrogenase (MDH, EC 1.1.137) catalyzes the reversible reduction of oxaloacetate to malate in the presence of NADH. Its existence as separate isoenzymes in the cytosol and in the mitochondria is associated with the function of a shuttle system (the malate-aspartate shuttle) for the transport of reducing equivalents from the cytosol into the mitochondria. Investigations of whether or not the enzymes in the malate-aspartate shuttle of tumor tissues are structurally and functionally identical to those of normal tissues have identified an aberrant cytoplasmic malate dehydrogenase in human tissues (Table 1) and serum of patients (Table 2) with malignant neoplasms as well as in Novikoff hepatoma cells, Morris minimal deviation hepatoma (H5123) and ethionine-induced hepatoma. Whereas the $K_m$ for oxaloacetate of the cytoplasmic MDH from normal human liver extracts is 40 uM, the $K_m$ value of the aberrant enzyme is characteristically about 1 mM.

GENERAL STATEMENT OF INVENTION

The determination of increased LD-5 activity may reflect the breakdown of tissue having high rates of glycolysis. It is carried out routinely on the serum, the pleural fluid or the ascitic fluid of patients with metastatic or primary neoplasm in the thorax or abdomen. The appearance of an increased LD activity in pleural fluid or ascitic fluid requires the measurement of inhibition of LD by pyruvate to determine the subunit content of LD. The presence of increased LD activity in pleural fluid or ascitic fluid also requires the measurement MD activity for the aberrant isoenzyme. The aberrant MD activity is thought to be related to the mechanism of increased glycolysis with increased LD-5 activity.

A Lineweaver-Burk plot of the cytoplasmic malate dehydrogenase activity from rat liver may be drawn as a function of oxaloacetate concentration. Preferably assay mixtures contain 0.14 mM NADH, and the appropriate amounts of oxaloacetate and enzyme in 0.1M phosphate buffer, pH 7.0. A similar plot may be made using human liver or rat Novikoff hepatoma tissue. A similar plot may be made using human adenocarcinoma tissue.

DETAILED DESCRIPTION OF THE INVENTION

Malate dehydrogenase (MDH, EC 1.1.1.37) catalyzes the reversible reduction of oxaloacetate to malate in the presence of NADH. In eukaryotic cells the enzyme is generally found to be present as two distinct isoenzymes; one form is present in the cellular cytosol and the other is present exclusively in the mitochondria. These two isoenzymes form part of a shuttle system (the malate-aspartate shuttle) that functions as the major mechanism for the transportation of reducing equivalents from the cytosol into the mitochondria.

As part of the ongoing studies on the mechanism of action and metabolic function of the malate dehydrogenases (1-3) we recently investigated the kinetic properties of the two isoenzymes present in rat Novikoff hepatoma tissues. These studies were initiated to evaluate whether or not the enzymes in the malate-aspartate shuttle of tumor tissues are structurally and functionally identical to those of normal tissues.

The inhibition of LD activity by pyruvate is described in the procedure requiring the comparative assay at 5 mM and 0.34 mM pyruvate. Inhibition of LD activity of less than 35% is indicative of predominantly LD-5 isoenzyme activity.

The unusual cytoplamic MD can be demonstrated by performing two assays: one at an oxaloacetate concentration of 0.33 mM and the other at an oxaloacetate concentration of 6.6 mM. Both substrate concentrations are well above the Km of the normal cytoplasmic MD and the rate of NADH oxidation should be independent of the oxaloacetate concentration. Therefore, the ratio of the two rates should be close to unity. When such assays were done on the sera of about 20 healthy individuals values between 0.8 and 1.0 were obtained for the two assays. The ratios were between 2.0 and 3.0 in assays of sera from patients with malignant neoplasm (Table 2) indicating the presence of an enzyme with a high Km value for oxaloacetate.

The analysis of serum samples for MD activity combined with the analysis of LD-5 activity appears to be a potentially useful tool in the diagnosis of malignancy.

EXAMPLES

Fresh tumor or liver tissue was homogenized with a glass tissue homogenizer in 0.1M potassium phosphate buffer, pH 7.5, containing 0.25M sucrose. The homogenate was centrifuged for 10 min at 10,000 xg to remove tissue debris. The supernatant was then centrifuged for 30 min at 20,000 xg to obtain a highspeed supernatant that contains the cytoplasmic enzymes. The supernatant did not contain any isocitrate dehydrogenase activity or transhydrogenase activity and was therefore judged to be free of mitochondrial enzymes. This high-speed supernatant was used without further fractionation for the experiments described below.

A determination of the $K_M$ values for the cytoplasmic enzyme yielded the values listed in Table 1. The $K_M$ values of the mitochondrial enzyme from the hepatoma tissue are identical with the values obtained with the enzyme from normal liver mitochondria. The cytoplasmic enzymes also have identical $K_M$ values for the coenzyme; however, the Lineweaver-Burk plots for the substrates were non-identical. Whereas the $K_M$ value for oxaloacetate obtained with the liver enzyme is approximately 55 μM, a Lineweaver-Burk plot obtained with the hepatoma enzyme displays two slopes. One of the slopes corresponded with a $K_M$ value that is approximately identical to that of the liver enzyme, whereas the other slope yielded a $K_M$ value for oxaloacetate of about 1 mM. A similar phenomenon was observed when malate was used as the substrate; however, the difference between the two slopes was less extensive than with oxaloacetate.

TABLE 1

Km FOR OXALOACETATE IN TISSUE HOMOGENATES OF HUMAN ORIGIN

| Tissue | Km (mM) |
| --- | --- |
| Adenocarcinoma of breast | 1.0, 1.2 |
| Adenocarcinoma of colon | 1.0 |
| Adenocarcinoma of uterus | 1.0 |
| Lymphocytic leukemia | 1.1 |
| Squamous cell carcinoma of larynx | 0.9 |
| Normal liver | 0.04 |

TABLE 2

SERUM FROM PATIENTS WITH CANCER

| Neoplasm | Km | Ratio* |
| --- | --- | --- |
| Lymphocytic leukemia | 0.90 | 2.0 |
| Adenocarcinoma, metastatic, liver | 1.1 | 2.1 |
| Adenocarcinoma, colon | 1.0 | 2.1 |
| Adenocarcinoma, ovary | 1.0 | 2.0 |
| Normal | 0.05 | 1.0 |

*Ratio = Reaction velocity at 6.8 mM OAA divided by velocity at 0.34 mM OAA

Novikoff hepatoma tissue contains two cytoplasmic enzymes that possess MD activity, one of which closely resembles that present in the rat liver cytoplasm. The other enzyme, having a $K_M$ of about 1 mM is not found in normal liver tissue.

In order to determine whether the normal cytoplasmic MD activity in the hepatoma tissue was due to a contamination of the tumor tissue with normal tissue, we purified the Novikoff hepatoma cells by growing them in tissue culture using a Dulbecco's modified essential medium, and transferring the culture until only neoplastic cells could be detected in the culture. An extract of these cells was subsequently used for the determination of the cytoplasmic MD activity. It appears thus that hepatoma cells contain the aberrant cytoplasmic MD in addition to the normal enzymes.

An extensive search for the presence of the aberrant enzyme in any normal rat tissue yielded negative results. The presence of the unusual enzyme was detected, however, in extracts of fetal rat liver. The data obtained thus far suggest that the enzyme with the low affinity for oxaloacetate is present during the early fetal stages, but gradually disappears during the gestation period. None of the aberrant enzyme appears to be present in the livers of newborn rats.

The same differences in catalytic properties were found when the MD of Sprague Dawley and Buffalo livers were compared with the hepatoma H5123 (Morris minimal deviation) and hepatoma 19 (ethionine-induced rapidly growing tumor) and the uninvolved liver controls from the same animals. In these experiments, typically, oxaloacetate saturation was not achieved below 3.5-7 mmol/l for maximum MD activity of the tumor. These changes were also observed in the virus induced leukemia of the hamster.

A cytoplasmic MD with characteristics similar to those of the aberrant MD is also present in various human tumors. The various types of neoplasia thus far investigated that contain the unusual MD are listed in Table 2. The unusual enzyme was absent in extracts of a granuloma and a fibroma. The latter tissues yielded double reciprocal plots with a single slope that closely resembles that obtained with extracts from normal liver tissues. The $K_M$ for oxaloacetate of the cytoplasmic MD from normal human liver extracts was found to be 40 mM. Double reciprocal plots of the data obtained from all other tissues listed in Table 1 yielded two slopes. The $K_M$ value of the aberrant enzyme is again about 1 mM.

The unusual cytoplasmic MD can also be detected in the serum of animals and patients with neoplastic disease. To demonstrate this two assays were done; one at an oxaloacetate concentration of 0.33 mM and the other at an oxaloacetate concentration of 6.6 mM. Both substrate concentrations are well above the $K_M$ of the normal cytoplasmic MD and the rate of NADH oxidation should be about independent of the oxaloacetate concentration. Therefore the ratio of the two rates should be close to unity. When such assays were done on the sera of about 20 healthy individuals values between 0.8 and 1.0 were obtained for the ratios of the two assays. Using sera obtained from patients with neoplastic disease we obtained ratios between 2.0 and 3.0, indicating the presence of an enzyme with a high $K_M$ value for oxaloacetate.

An analysis of serum samples for MD activity as described here could be a useful tool in the early diagnosis of certain malignant growths. In addition, the technique could be used to evaluate the effectiveness of various therapeutic treatments as well as of the surgical removal of a malignancy.

Two possibilities deserve consideration. The first possibility is that the activity represents a hitherto unknown MD isoenzyme that is only present during embryonic development and in certain neoplasms. It is very difficult to see, however, how the presence of a MD isoenzyme with a very high $K_M$ for oxaloacetate can provide a metabolic advantage to rapidly growing cells. If this is the case then the non-specific dehydrogenase must be present in much higher concentrations in tumor tissues than in normal tissues, since we could not detect the enzyme in normal tissue extracts. Lactate dehydrogenase would be a likely candidate since it is closely related to MD in many respects. We therefore assayed several tumor extracts as well as normal tissue extracts for lactate dehydrogenase activity. Although we found a somewhat increased level of lactate dehydrogenase in the tumor tissue extracts, the differences could not possibly explain the aberrant MD activity present in the tumors.

In a preferred embodiment of the invention a method is provided of measuring an MD activity derived from malignant tissues and body fluids by measuring the reduction of its oxidized substrate oxaloacetate, in two different conditions, which favors either the total activity for normal MD or an increased MD activity for aberrant MD of malignancy, depending only on the concentration of oxidized substrate and the amount of aberrant MD activity present including, preparing a first solution made up of a predetermined amount of NADH and a first concentration of oxidized substrate, adding said body fluid containing isoenzymes to the solution to bring the first solution to a final concentration equal to a dilution adjusted concentration of the oxidized substrate, measuring the adjusted first activity of the first solution, preparing a second solution of an amount of NADH equal to the first predetermined amount of NADH and the oxidized substrate to a second concentration of 10 to 20 times the first concentration, adding the body fluid containing isoenzymes to the second solution to a dilution adjusted concentration equal to the first concentration, measuring the second activity of the second solution, comparing the first activity to the second concentration (activity) to obtain a ratio of activities relative to the two activities with the first activity in the denominator and the second activity in the numerator, determining the amount of MD activity in the numerator, determining the amount of MD activity enhancement (accelerated activity) by observing the ratio of measured MD activities.

In another preferred embodiment of the invention a method is provided of measuring isoenzymes selected from the group consisting of lactate dehydrogenase and malate dehydrogenase in body fluids, this method being adapted for use in automated instruments and operable without preincubation, the method including, (a) containing a first portion of a body fluid sample suspected of containing the isoenzymes with a reagent composition containing an oxidized substrate selected from the group consisting of pyruvate and oxaloacetate and nicotinamide-adenine dinucleotide under conditions suitable for enzymatic activity and at a controlled pH of 7.5 or less wherein the oxidized substrate and nicotinamide-adenine dinucleotide are present in non-rate limiting amounts, (b) measuring the enzymatic activity of the first portion to obtain a first measurement, (c) contacting a second portion of the body fluid with a reagent composition containing the oxidized substrate and nicotinamide-adenine dinucleotide under conditions suitable for enzymatic activity and at a controlled pH of approximately 7.5, wherein the oxidized substrate is present in an amount at least ten times the amount of step (a) and the enzyme concentration is approximately the same as step (a), (d) measuring the enzymatic activity of the second portion to obtain a second measurement, (e) comparing the first activity to the second concentration (activity) to obtain a ratio of activities relative to the two activities with the first activity in the denominator and the second activity in the numerator, determining the amount of MD activity enhancement (accelerated activity) by observing the ratio of measured MD activities.

In each of these preferred embodiments it is preferred that the first concentration is 0.15 to 0.5 millimoles per liter of NADH solution, and that the ratio of MD activities is 1.5–2.5 for the presence of malignant MD. Normally this ratio is not greater than 1.0 in normal patients.

I claim:

1. A method of indicating the presence of neoplastic tissue in a patient comprising:
   (a) providing a body fluid from said patient,
   said body fluid comprising cytoplasmic malate dehydrogenase,
   (b) determining whether said body fluid comprises aberrant malate dehydrogenase by determining the Kms using oxaloacetate,
   whereby the presence of aberrant malate dehydrogenase indicates the presence of neoplastic cells in said patient.

2. The method of claim 1, wherein said determining comprises measuring the ratio of Km for malate dehydrogenase at two oxaloacetate concentrations, one said concentration being substantially greater than the other, and both of said concentrations being above that needed to determine the Km for normal malate dehydrogenase, whereby a ratio of about two is an indication of neoplastic cells in the patient from which the body fluid is taken.

3. A method of indicating the presence of neoplastic tissue in a patient comprising:
   (a) providing a body fluid from said patient, said body fluid comprising cytoplasmic malate dehydrogenase,
   (b) determining whether said body fluid comprises aberrant malate dehydrogenase, said determining comprising reacting oxaloacetate using said cytoplasmic malate dehydrogenase,
   whereby the presence of aberrant malate dehydrogenase indicates the presence of neoplastic cells in said patient.

4. The method of claim 3 wherein said determining further comprises the use of NADH.

5. A method of indicating the presence of neoplastic tissue in a patient comprising:
   (a) providing body fluid from said patient, said body fluid comprising cytoplasmic malate dehydrogenase,
   (b) determining whether said body fluid comprises aberrant malate dehydrogenase,
   said determining comprising a reaction using said cytoplasmic malate dehydrogenase,
   whereby the presence of aberrant malate dehydrogenase indicates the presence of neoplastic cells in said patient.

* * * * *